United States Patent [19]

Hewitt

[11] Patent Number: 4,812,119
[45] Date of Patent: Mar. 14, 1989

[54] METHOD OF MIXING DENTAL IMPRESSION MATERIALS AND DEVICE THEREFOR

[76] Inventor: William B. Hewitt, 118 Springwater Dr., Columbia, S.C. 29223

[21] Appl. No.: 65,347

[22] Filed: Jun. 23, 1987

[51] Int. Cl.[4] .............................................. A61C 9/00
[52] U.S. Cl. ........................................ 433/49; 433/52; 433/215; 433/229; 366/602
[58] Field of Search ...................... 433/49, 79, 83, 229, 433/223, 215, 226, 228.1, 180, 213, 163; 108/20, 21, 50, 91, 139, 154; 366/602

[56] References Cited

U.S. PATENT DOCUMENTS

| | | | |
|---|---|---|---|
| 1,539,428 | 5/1925 | Romaine | 433/49 |
| 1,729,292 | 9/1929 | McCarthy | 433/49 |
| 1,993,450 | 3/1935 | Lowry | 433/49 |
| 2,264,128 | 11/1941 | Branch | 108/139 |
| 2,527,969 | 10/1950 | Siebenkittel | 108/20 X |
| 3,448,701 | 6/1969 | Cordova | 108/20 |
| 3,753,291 | 8/1973 | Bocian et al. | 433/52 |
| 4,555,900 | 12/1985 | Egawa | 108/20 |

Primary Examiner—Larry Jones
Attorney, Agent, or Firm—Needle & Rosenberg

[57] ABSTRACT

A method and a device for mixing dental impression materials comprising a motor-driven rotatable turntable with two mixing plates which are successively and detachably secured thereon. The components of thick and thin viscosity, elastomeric dental impression materials are homogeneously mixed together, respectively, on each of the plates as those plates are independently rotated on the turntable.

6 Claims, 3 Drawing Sheets

METHOD OF MIXING DENTAL IMPRESSION MATERIALS AND DEVICE THEREFOR

BACKGROUND OF THE INVENTION

The current method of mixing elastomeric dental impression materials generally employed in the taking of dental impressions is accomplished with the use of a mixing surface, i.e. a rectangular flat pad, which remains stationary on a table top, and a hand held mixing spatula. The two components of the impression material, i.e. base and catalyst, are expressed onto the mixing pad, usually in equal amounts. The operator then incorporates the base and catalyst, using the hand held spatula, until a homogeneous mix is obtained. This first batch of impression material is then loaded into a syringe device, which is then handed to the dentist, who applies the material to a prepared tooth.

The operator then begins mixing a second batch of elastomeric impression material, which is generally more viscous, for use in an impression tray. The second batch is incorporated in the same way as the first batch after homogeneous incorporation, that is, by scraping the impression material from the mixing pad with the spatula and placing the impression material in a tray. The loaded tray is then handed to the dentist for placement into the patent's mouth.

The disadvantage of this old method of mixing dental elastomeric impression materials is the time required to obtain, by hand mixing, a completely homogeneous mix. This increased mixing time of the old method effectively decreases the working time in taking a dental impression for the dentist and, therefore, increases the likelihood of obtaining an unacceptable impression.

A further disadvantage of the prior method is that it is extremely difficult to obtain a completely homogeneous mix of impression material due to the substantial amount of physical effort required. Often this leads to incomplete mixes and results in unpolymerized areas of the impression material. If that area happens to come in contact with a critical area of the impression, an inaccurate stone die may result, and hence a cast restoration which will not seat on a prepared tooth, rendering it useless to the patient and a financial loss to the dentist.

Usually approximately one-half of the elastomeric dental impression material dispensed for an impression under the current method is left on the mixing pad after the syringe and tray are loaded. Since most elastomeric impression materials are quite costly, this constitutes an obvious waste. Also, the current method of mixing, loading, and delivering elastomeric impression materials is inexact and usually results in excess impression material spilling onto the table, dental assistant, dentist and patient. This creates quite a mess and can lead to permanently stained clothing and equipment.

SUMMARY OF THE INVENTION

The above disadvantages are overcome by the present invention which includes a turntable, a means of rotating the turntable and first second mixing surfaces which are successively and detachably secured to the top of the turntable. The two components each of thin and thick viscosity elastomeric dental impression materials are placed, respectively, on the first and second mixing surfaces and the surfaces are successively placed on the turntable. As the mixing surfaces are rotated, the operator manipulates the components with a spatula until a homogeneous mixture of each of the impression materials is obtained.

While the respective mixing surfaces continue to rotate with the respective mixtures thereon, the operator inclines the open back of an impression material injection syringe or of an impression tray syringe to the rotating impression mixture to force the respective mixture into the respective syringe. Thus, while the dentist is applying to the patient's teeth the thin viscosity impression material via its loaded syringe, the batch of thick viscosity material can be prepared, its syringe loaded and the contents injected into the trough of an impression tray which the dentist can then apply to the patient's teeth immediately after the thin viscosity material has been placed on the teeth.

The device of the present invention mixes elastomeric dental impression materials much faster and more efficiently than the old method. Decreasing the mixing time thus allows more working time for the dentist, resulting in a more accurate impression and reducing stress on the dentist. The device also mixes the two components of elastomeric impression material more homogeneously, which is extremely important. Hand mixing, the old method, rarely results in a truly homogeneous mixture, thus compromising the accuracy of the impression.

The use of the present invention enables the operator to use up to 50% less impression material as compared with the old manual method, thus resulting in a significant savings on impression materials, which are generally quite costly. Another advantage which this invention has over the old method is that it is less messy due to the increased managability of the impression materials. This enables the operator to keep a neat working area and prevents accidental contact of the impression material with clothing and equipment, which could become permanently stained by certain impression materials.

The utilization of the present invention in the mixing of any two-paste base and catalyst impression material incorporates much less air than with the traditional hand-mixed method. The incorporation of air in an elastomeric dental impression material significantly contributes to altering the dimensional stability of the impression material. Significant quantities of air are entrapped in impression material mixed by the hand method. The unpolymerized impression material containing large quantities of air typical of the hand-mixed type, upon being introduced during an impression taken on a patient, is raised in temperature to approximately 85° F. prior to polymerization and removal from the mouth. By the time the die stone is poured into the impression, the tray and impression material contained therein cools down to room temperature. This represents a temperature change of at least 15° F. The dimensional change of an impression material due to temperature change without air is clinically negligible. However, that same impression material will undergo significant dimensional change due to temperature change proportional to air content. Therefore, an impression material that has as little air as possible will be much more accurate than the same impression material that has relatively much more air. Impression material mixed using the present invention contains less air than the same material mixed by hand. This translates into a significantly more accurate dental impression and hence a more accurate final restoration.

In general, the use of this device results in less stress on the dental assistant, because it enables the assistant to mix dental impression materials more consistently and in less time, using less effort than the old manual method.

BRIEF DESCRIPTION OF THE FIGURES OF THE INVENTION

DETAILED DESCRIPTION OF AN ILLUSTRATIVE EMBODIMENT

Figure 1:
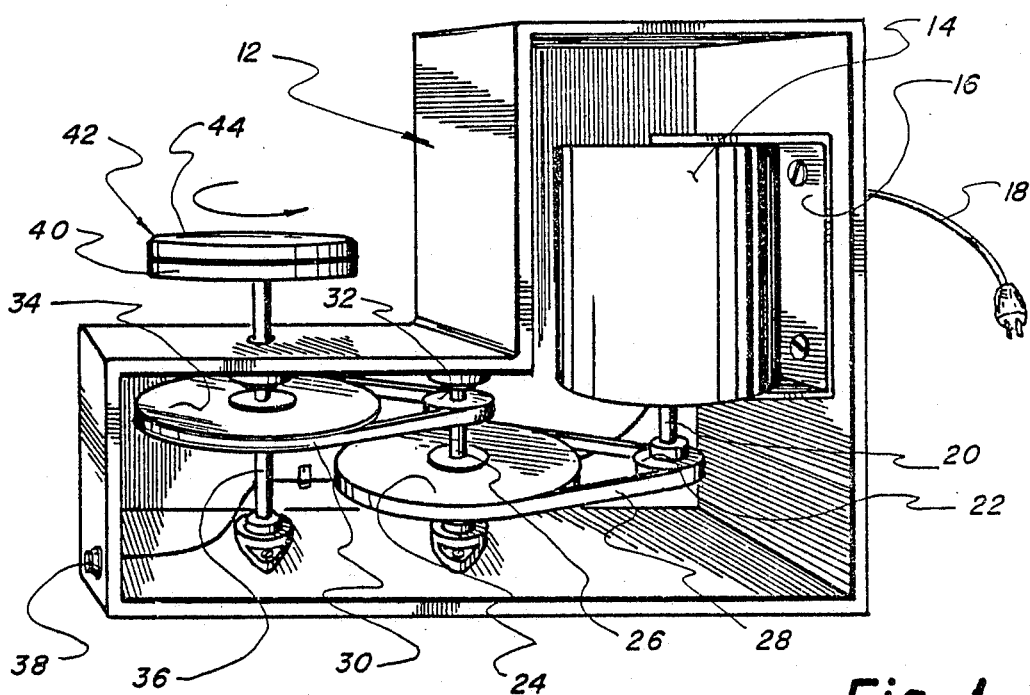
FIG. 1 is a perspective view of the rear of the mixing device of the present invention.
Figure 2:
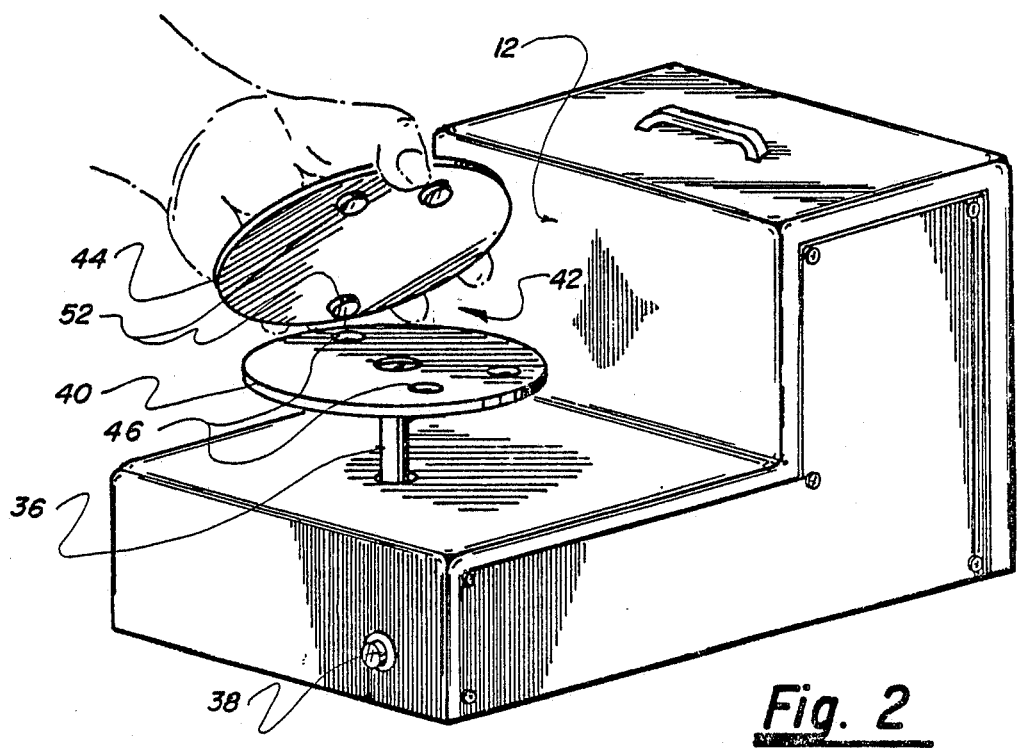
FIG. 2 is a perspective view of the front of the mixing device showing the detachable feature of the mixing surface from the turntable.
Figure 3:
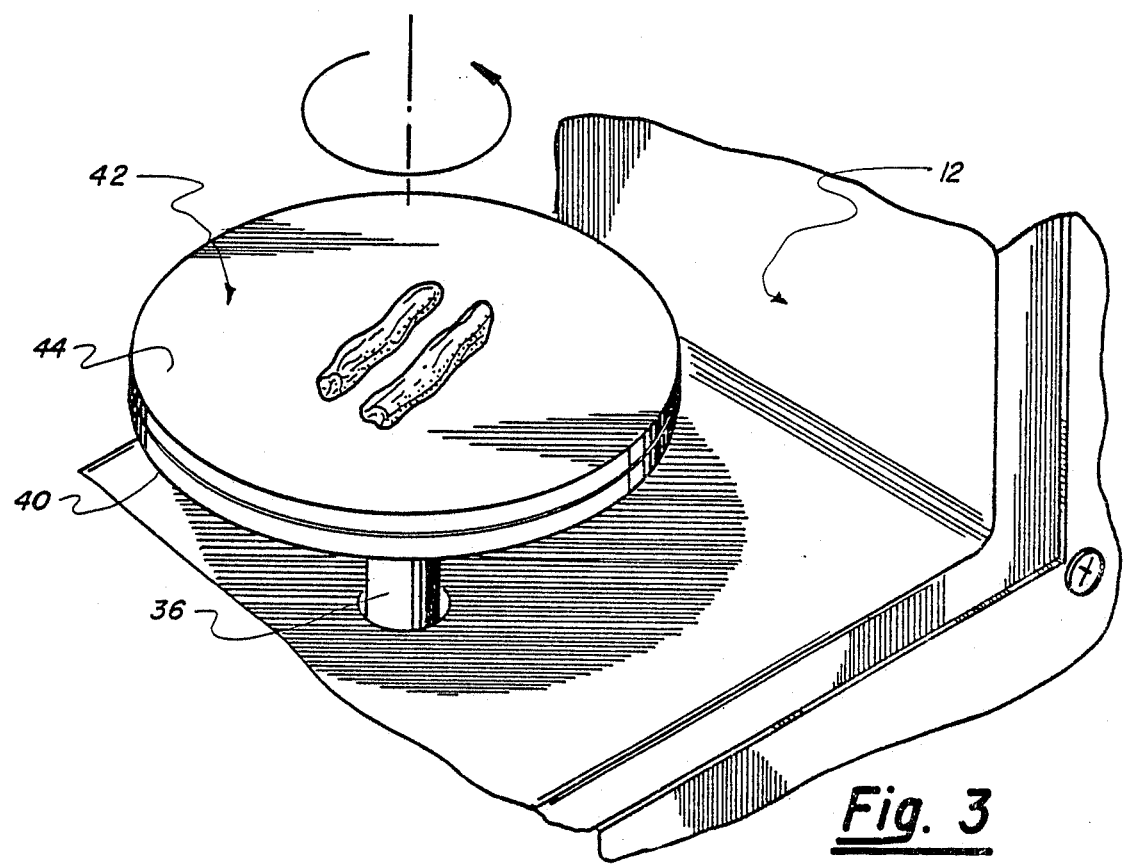
FIG. 3 is a perspective view of the two components of an elastomeric impression material on a mixing surface.
Figure 4:
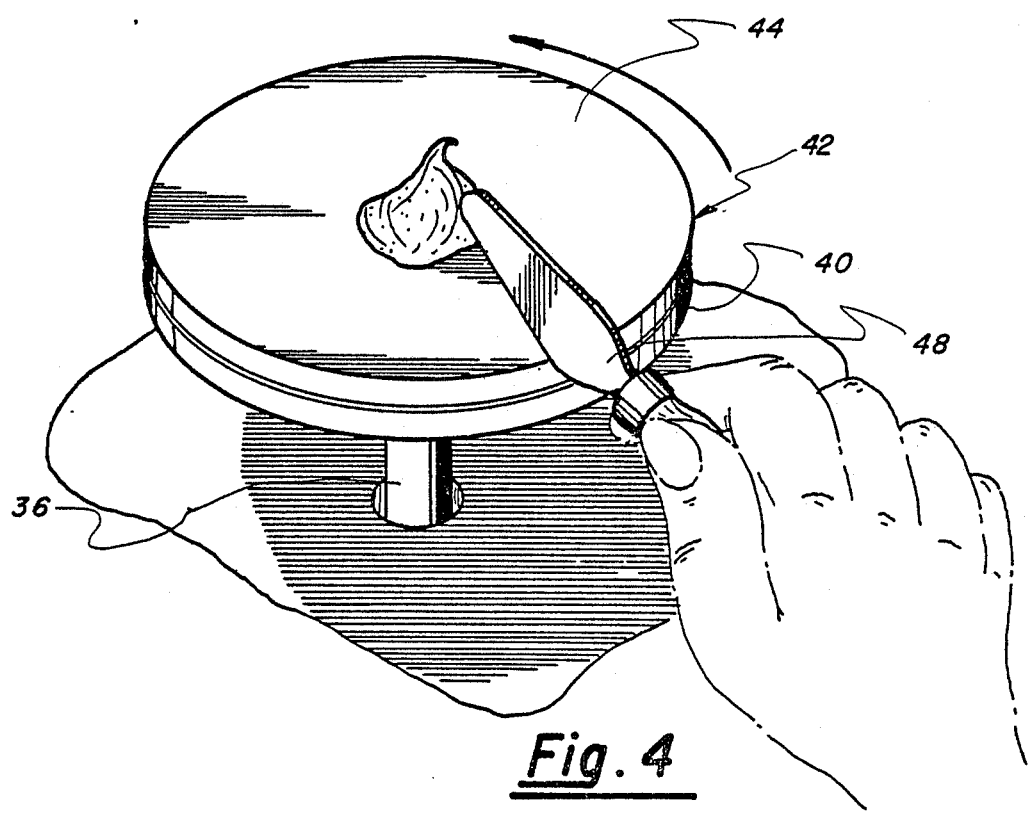
FIGS. 4 and 5 are perspective views which illustrate how the hand held spatula creates a homogeneous mixture of the components of FIG. 3 while the mixing surface is rotated.
Figure 5:
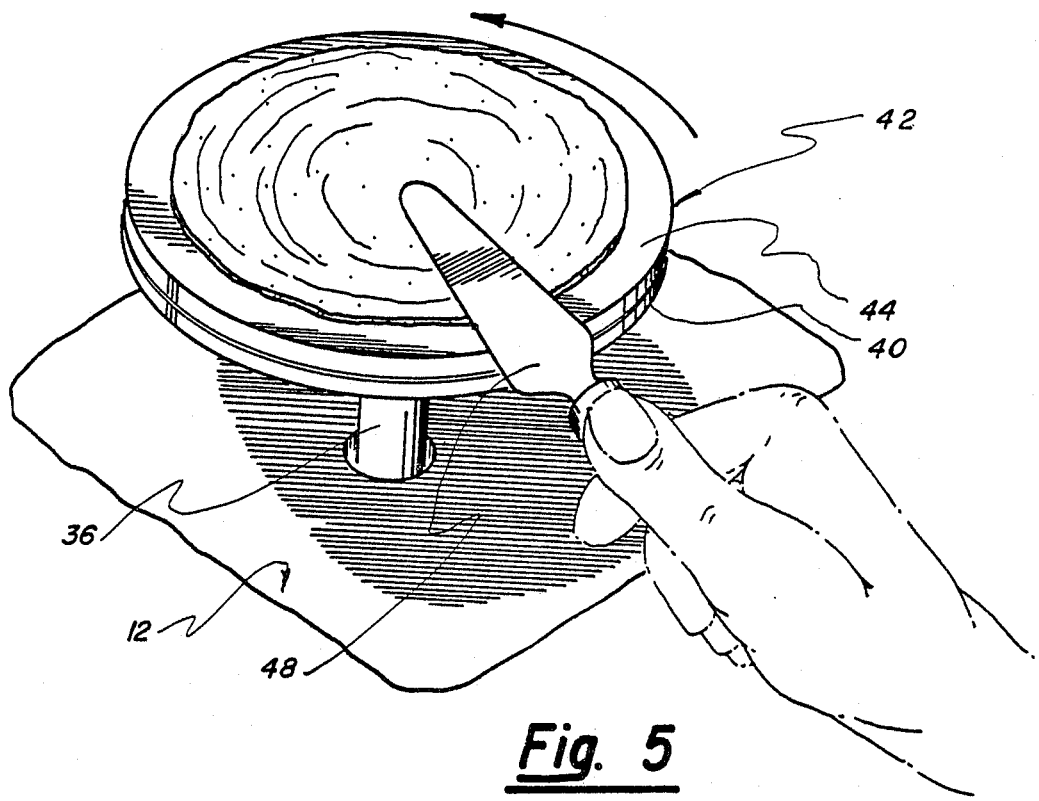
Figure 6:
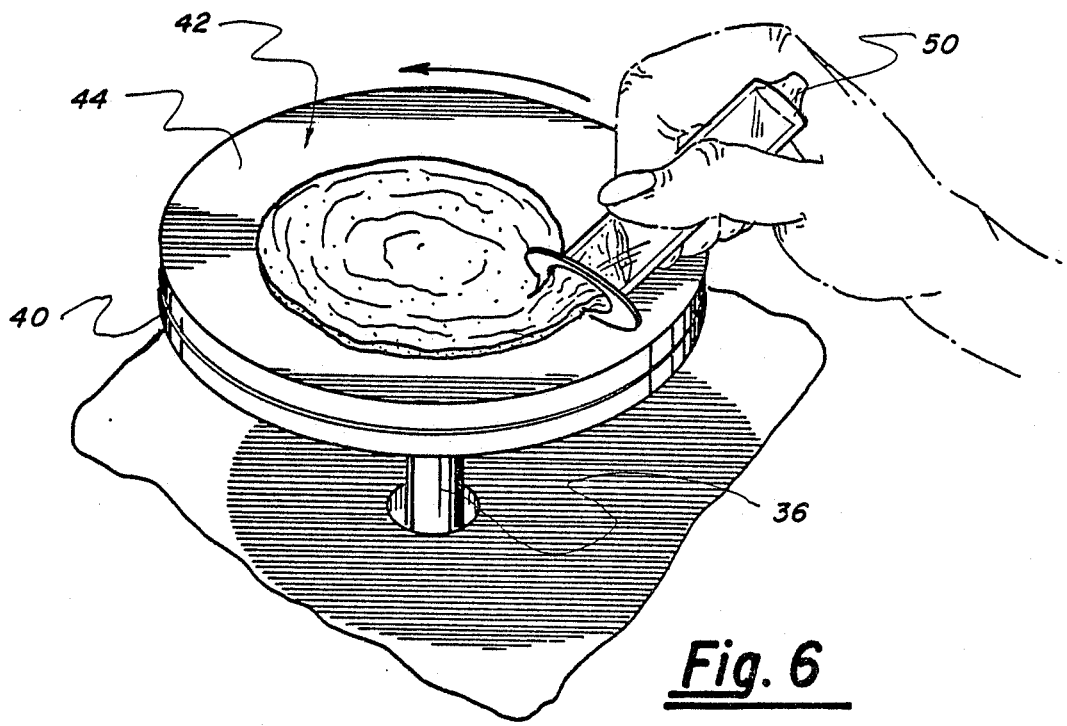
FIG. 6 is a perspective view of the loading of a syringe with the impression mixture.

Referring to FIGS. 1 and 2, the present invention 10 comprises an L-shaped housing 12 which has a conventional electric motor 14 and which is connected to a power source (not shown) by means of cord 18. The specific overall appearance of the housing 12 is not critical to the invention 10.

A drive shaft 20 with a first pulley 22 thereon extends downwardly from the motor 14 and is connected to a second pulley 24 mounted on rotatable shaft 26 by means of first belt 28. A second belt 30 interconnects third pulley 32 on shaft 26 with fourth pulley 34 that is secured onto output shaft 36 which is journaled at is bottom for rotational movement about a vertical axis and which extends through an opening in the top of housing 12. A thumb switch 38 on the front of housing 12 controls the motor 14.

The motor and associated shafts, pulleys and belts which comprise the reduction gear assembly are not critical to the present invention 10. The desired direction of rotation, torque and speed of rotation of output shaft 36 may be achieved by any conventional means.

As seen in detail in FIG. 2, a circular, flat turntable 40 is mounted on the top of output shaft 36 and detachably receives thereon a round, first mixing surface which comprises a plate or slab 42, that is preferrably made of glass. The top 44 of plate 42 should be smooth, flat and non-resilient. It has been found that the preferable diameter of plate 42 is 5¾ inches; a smaller diameter would not allow the volume of impression material usually needed to be mixed and a larger diameter would be physically cumbersome to handle, both in interchanging during the mixing process (as described hereinbelow), as well as physically limiting for most individuals during the manipulation of the impression materials with the spatula.

Means is provided for detachably mounting the plate 42 to the turntable 40. As shown, it includes a plurality dowels 52, or pins that depend from the bottom of a plexiglass slab (not shown) that is glued to the bottom of the plate 42. The dowels 52 are in registry with openings 46 in the top of the turntable 40. When the dowels 52 are inserted into the openings 46, the plate 42 cannot be separated from the turntable 40 unless the plate 42 is lifted upwardly.

A preferred requirement for the present invention 10 is to have the plate 42 be quickly disengaged from the turntable 40 with one hand and interchanged with an identically constructed mixing plate (not shown).

Two mixing plates are needed due to the use of two viscosities of elastomeric impression materials usually employed to take a dental impression. Since the technique used to mix both viscosities of impression material requires the second batch be mixed immediately after the first, the first mixing plate 42 must be disengaged from the turntable 40 and replaced with the second mixing plate in a matter of 2 or 3 seconds, using one hand. The construction of the two-piece turntable and mixing plates device 10 facilitates this quick interchange of mixing plates.

In the operation of the device 10, the elastomeric impression material, thin viscosity, base and catalyst is dispensed onto the first mixing plate 42, usually in equal amounts or equal lengths per manufacturer's instructions. These are not allowed to come into contact with each other until the mixing has begun. The first mixing plate 42 is then placed into engagement with the turntable 40 by having the dowels 52 engage the openings 46. The base and catalyst components of an elastomeric impression material, thick viscosity, are dispensed onto the surface of the second mixing plate, usually in equal amounts and not allowed to come in contact with each other. This second mixing plate, containing the base and catalyst thick viscosity, is placed aside within reach of the operator.

When the dentist indicates to the mixing operator that he is ready to take the impression and begin mixing, the operator turns the device on by depressing the thumb switch 38. The turntable 40 will turn counter clockwise. Optionally, of course, the turntable 40 can be designed to rotate clockwise to provide manipulation of the impression materials by left-handed operators. A hand spatula 48 is then placed against the rotating plate 42 and a series of compressive and deflective maneuvers result in the complete homogeneous incorporation of base and catalyst of the thin viscosity material, usually within 15 to 20 seconds. The last maneuver in the mixing process of the thin viscosity involves deflecting the spatula 48 on the mixing plate 42 such that rotation of the plate 42 causes the impression material to become evenly distributed in a flat coat over the entire surface 44.

While the mixing plate 42 is still rotating, the impression material injection syringe 50, with the plunger removed (not shown), is placed back down against the rotating surface 44 of the mixing plate 42, starting at the outer periphery of surface 44. The longitudinal axis of the impression syringe 50 is tilted 10° from perpendicular to the surface 44 in the direction of turntable rotation. With the open back of the impression syringe 50 held against the rotating mixing plate 42 in this manner, the homogeneously mixed impression material is forced into the back of the impression syringe 50. To fully load the impression syringe 50 and clear the mixing surface 44 of the impression material, the back of the impression syringe 50 is translated toward the center of the mixing plate 42 while rotation of the turntable 40 occurs.

After the impression syringe is loaded, the impression syringe plunger is placed in the back of the open barrel of the syringe 50 and handed to the dentist. While the dentist is applying the thin viscosity impression material via the syringe 50, to the indicated teeth, the mixing operator stops the rotation of the turntable 40 and quickly disengages the first mixing plate 42 and interchanges it with the second mixing plate containing the thick viscosity base and catalyst impression material. The operator then turns the device 10 on again and, with a second clean spatula, incorporates the second batch of thick viscosity impression material in the same manner as the first batch.

After the second batch is homogeneously mixed, it is, similar to the first batch, loaded into a second, larger, impression tray syringe (not shown). The plunger is placed in the back of this second syringe after it is filled with impression material. The operator then depresses the plunger of the tray syringe and forces the thick viscosity impression material out the front end of the tray syringe into the entire trough of an impression tray (not shown), filling it evenly. Once the impression tray is properly filled, it is then handed to the dentist by the mixing operator for placement into the patient's mouth. Normally, the entire mixing process, from the start of incorporation of the first viscosity to the seating of the tray of impression material in the patient's mouth, can be easily achieved with ninety (90) seconds.

What I claim is:

1. A device for mixing dental impression material comprising:
   (a) a fixed mixing surface comprising a plate constructed of non-resilient material;
   (b) means for rotating said surface; and
   (c) means for detachably securing said first surface to said rotating means whereby a plurality of first dental impression materials may be homogeneously mixed together on said first surface as the operator manually manipulates said materials, said securing means comprising a plurality of pins on a selected one of said plate or said turntable and a plurality of openings in registry with said pins in the other of said plate or said turntable.

2. A device as claimed in claim 1 and further comprising a second mixing surface that is detachably secured to said rotating means after said first mixing surface is removed therefrom for homogeneously mixing thereon a plurality of second dental impression materials.

3. A device as claimed in claim 1, wherein said rotating means comprises a turntable, drive means and means for interconnecting said turntable with said drive means whereby said turntable is rotated about a vertical axis.

4. A device as claimed in claim 1, wherein said means for rotating said surface rotates said surface in both clockwise and counterclockwise directions.

5. A method of preparing a dental impression, comprising the steps of:
   (a) applying a plurality of first dental impression materials to a first surface that is detachably secured to a turntable;
   (b) rotating said first surface and said turntable for a predetermined amount of time;
   (c) incorporating together said materials as said surface is rotated so that a homogeneous first mixture of said materials is obtained;
   (d) stopping the rotation of said first surface and said turntable;
   (e) removing said first surface;
   (f) installing a second surface on said turntable;
   (g) repeating steps a-e for a second surface and plurality of second dental impression materials which are mixed thereon to form a homogeneous second mixture; and
   (h) utilizing said first and second mixtures to obtain an impression of a patient's teeth.

6. A method as claimed in claim 5 including the step of loading said first and second mixtures into respective first and second impression syringe applicators prior to said stopping steps.

* * * * *